(12) United States Patent
Emerson, Jr. et al.

(10) Patent No.: US 7,968,527 B2
(45) Date of Patent: Jun. 28, 2011

(54) INHIBITION OF FGF SIGNALING

(75) Inventors: Charles P. Emerson, Jr., Winchester, MA (US); Xingbin Ai, Watertown, MA (US)

(73) Assignee: Boston Biomedical Research Institute, Watertown, MA (US)

( * ) Notice: Subject to any disclaimer, the term of this patent is extended or adjusted under 35 U.S.C. 154(b) by 796 days.

(21) Appl. No.: 11/057,390

(22) Filed: Feb. 11, 2005

(65) Prior Publication Data

US 2005/0227921 A1 Oct. 13, 2005

Related U.S. Application Data

(60) Provisional application No. 60/544,449, filed on Feb. 13, 2004.

(51) Int. Cl.
*C12N 5/00* (2006.01)
*C12N 9/14* (2006.01)
*A61K 31/727* (2006.01)
*A61K 38/00* (2006.01)

(52) U.S. Cl. ....... 514/56; 514/13.3; 514/19.2; 514/19.3; 435/183; 435/375

(58) Field of Classification Search .................. None
See application file for complete search history.

(56) References Cited

U.S. PATENT DOCUMENTS 7,129,072 B1 * 10/2006 Schlessinger et al. ........ 435/194
2003/0147875 A1 * 8/2003 Rosen et al. .................. 424/94.6

FOREIGN PATENT DOCUMENTS

WO WO 00/74634 A2 12/2000
WO WO 03/012053 A2 2/2003

OTHER PUBLICATIONS

Esner et al., Int. J. Dev. Biol., 2002, 46:817-825.*
Bellosta et al., Mol. Cell. Biol., 2001, 21(17):5946-5957.*
Lai et al., J. Biol. Chem., 2003, 278(25):23107-23117.*
Itoh et al., Dev., 1994, 120:2703-2711.*
Lai et al., Gastroenterology, Jan. 2004, vol. 126(1):231-248. (see Abstract).*
Morimoto-Tomita et al., J. Biol. Chem., 2002, vol. 277(51):49175-49185.*
Jinping Lai et al, Loss of HSulf-1 Up-Regulates Heparin-binding Growth Factor Signalaing in Cancer, The Journal of Biological Chemistry, Jun. 20, 2003, vol. 278, No. 25, p. 23107-23117.
J. Lai, Loss of Hsulf-1 Up-regulates Heparin-binding Growth Factor Signaling in Cancer, J. Biol. Chem. 278(25): 23107-23117 (Jun. 2003).
J.P. Lai et al., hSulfl Sulfatase Promotes Apoptosis of Hepatocellular Cancer Cells by Decreasing Heparin-binding Growth Factor Signaling, Gastroenterology 126(1): 231-248 (Jan. 2004).
J. Morimoto-Tomita et al., Cloning and Characterization of Two Extracellular Heparin-degrading Endosulfatases in Mice and Humans, J. Biol. Chem. 277(51): 49175-49185 (Dec. 2002).
X. Ai et al., Substrate Specificity and Domain Functions of Extracellular Heparan Sulfate 6-O-Endosulfatases, Qsulf1 and Qsulf2, J. Biol. Chem. 281(8): 4969-4976 (Feb. 2004).
K. Narita et al., Hfulf-1 Inhibits Angiogenesis and Tumorigenesis In vivo, Cancer Res. 66(12): 6025-6032 (Jun. 2006).
Ishibara, M., Structural requirements in heparin for binding and activation of FGF-1 and FGF-4 are different from that for FGF-2, Glycobiology, vol. 4, No. 6 pp. 817-824, 1994.
Lai, et al., "hSulf1 Sulfatase Promotes Apoptosis of Hepatocellular Cancer Cells by Decreasing Heparin-Binding Growth Factor Signaling", Gastroenterology 2004; 126:231-248.
Guimond, et al., "Activating and Inhibitory Heparin Sequences for FGF-2 (Basic FGF)", Journal of Biological Chemistry, vol. 268, No. 32, Nov. 15, pp. 23906-23914,1993.
Askikari-Hada, et al., "Characterization of Growth Factor-binding Structures in Heparin/Heparan . . . ", Journal of Biol.Chem., vol. 279, No. 13, Mar. 26, pp. 12346-12354, 2004.
Allen, et al., "Role of heparan sulfate as a tissue-specific regulator of FGF-4 and FGF receptor recognition", Journal of Cell Biol., vol. 155, No. 5, Nov. 26, 2001; 846-857.
Wu, et al., "The Involvement of Heparan Sulfate (HS) in FGF1/HS/FGFR1 Signaling Complex", Journal of Biol. Chem., vol. 278, No. 19, May 9, pp. 17121-17129, 2003.
Wang, et al., "QSulf1, a heparan sulfate 6-0-endosulfatase, inhibits fibroblast growth factor signaling . . . ", PNAS, Apr. 6, 2004, vol. 101, No. 14, 4833-4838.

* cited by examiner

*Primary Examiner* — Elizabeth C. Kemmerer
*Assistant Examiner* — Xiaozhen Xie
(74) *Attorney, Agent, or Firm* — Pierce Atwood LLP; Kevin M. Farrell; David J. Wilson

(57) ABSTRACT

Methods and compositions for inhibiting FGF signaling are described. Methods of the invention include contacting an FGF-responsive cell with exogenous heparan sulfate 6-O endosulfatase (Sulf1) in an amount effective to modify endogenous heparan sulfate, thereby inhibiting FGF signaling. Methods of the invention also include contacting an FGF-responsive cell with an exogenous Sulf1-modified compound, the exogenous Sulf1-modified compound being characterized by the ability to reduce binding of FGF2 or FGF4 to FGFR1. Compositions comprising exogenous Sulf1-modified compounds are also provided for use in conjunction with methods of the present invention.

13 Claims, 6 Drawing Sheets

INHIBITION OF FGF SIGNALING

RELATED APPLICATIONS

This application claims priority to Provisional Application No. 60/544,449 filed Feb. 13, 2004.

GOVERNMENT SUPPORT

This invention was made with Government Support under HD Grant Number 7 R 37 HD007796-33 awarded to C. Emerson, Jr. The Government has certain rights in the invention.

BACKGROUND OF THE INVENTION

Abbreviations footnote: HSPG, heparan sulfate proteoglycan; HS, heparan sulfate; FGF, fibroblast growth factor; FGF2, fibroblast growth factor 2, also known as bFGF; FGF4, fibroblast growth factor 4, also known as eFGF; GlcNR6Sase, GlcNR 6-O exosulfatase; FGFR1, FGF receptor 1; QSulf1, quail Sulf1; ERK, extracellular signaling regulated kinase.

HSPGs are extracellular matrix glycoproteins that regulate cell surface signaling during embryogenesis and pathophysiology of diseases. HSPGs include a protein core coupled to several covalently linked HS chains that bind to signaling molecules. HS chains are composed of 50-200 disaccharide repeats of uronic acid and glucosamine residues that are selectively sulfated at 2-O position of uronic acid and 6-O, 3-O, and N positions of glucosamine residues. The sulfation patterns of HS are further regulated to create highly sulfated and undersulfated domains along the length of the HS chain, leading to structural heterogeneity.

Sulfation of HS chains is required for developmental signaling processes in embryonic cells. Loss of HS sulfation in Drosophilia sulfateless and slalom mutants leads to defects in Wingless (Wg) and FGF or Wg and Hedgehog (Hh) signaling, respectively, and to defects in tissue patterning in the embryo. Further, sulfation deficiencies at individual positions within the HS disaccharide unit also cause signaling defects, as revealed in studies of mutations that disrupt HS biosynthesis. For example, mice with a gene-trap mutation in Hs2st, a key HS 2-O-sulfotransferase, lack 2-O sulfated uronic acid and exhibit lethal kidney agenesis due to defects in multiple signaling processes. RNAi inhibition of Drosophila HS 6-O-sulfotransferase gene expression reduces FGF signaling activity and disrupts the primary branching of the tracheal system. Consistent with these genetic studies, treatment of cells in culture with chlorate to inhibit HS sulfation results in defects in BMP, Wnt and FGF signaling. HS sulfation, therefore, plays important roles in multiple signaling activities in embryos. However, the biological mechanisms for regulating the sulfation states of HS in embryos and the biochemical roles of specific HS sulfate groups in the control of ligand activity and/or receptor interactions are not well understood.

Recently, a family of HS 6-O endosulfatases have been identified that modify HS 6-O sulfation and developmental signaling in embryonic cells, providing a new class of evolutionarily conserved regulators of HS sulfation. A second, closely related family member Sulf2 has been identified in mammals and birds. Sulf1 exhibits structural and enzymatic features distinct from known glucosamine 6-O sulfatases (GlcNR6Sase), which are lysosomal exosulfatases that catalyze the hydrolysis of terminal 6-O sulfo groups during HS degradation. In contrast, Sulf1 is secreted through the Golgi and is docked on the cell surface through its distinctive hydrophilic domain, and Sulf1 functions as a 6-O endosulfatase, with substrate specificity for trisulfated IdoA2S-GlcNS6S disaccharide units of HS/heparin. The avian ortholog, QSulf1, is required for Wnt-dependent gene expression in muscle progenitor cells of the quail embryo. QSulf1 activity remodels the 6-O sulfation states of cell surface HSPGs and decreases the binding affinity between Wnt ligand and HS.

Biochemical and crystallographic studies show that HS sulfation is required for FGF ligand-receptor interactions and FGF signaling. HS chains containing trisulfated disaccharide units greatly promote FGF2-FGFR1 binding and signaling, although FGF2 can bind to FGFR1 in the absence of HS in cell binding assays and in crystallographic studies. Among the sulfate groups on HS, sulfation at 6-O position of glucosamine residues is required for FGF2-FGFR1 and FGF4-FGFR1 interactions and signaling. Although distinct sequences and sulfation patterns in HS chains are required for FGF ligand and receptor binding, 6-O sulfation of HS is crucial for FGF signaling activity.

FGFs and FGFRs (FGF receptors) play critical roles in many developmental and disease processes including angiogenesis and cancer. Sulf1 is a cell surface 6-O HS endosulfatase expressed in embryonic cell lineages controlled by multiple signaling pathways including FGF, and recent studies reveal that the human Sulf1 ortholog, HSulf1, can down-regulate FGF-dependent ERK kinase activity in human cancer cells. The ability to regulate FGF-controlled developmental process in embryos through a more detailed understanding of these pathways would represent a significant advance in the art.

SUMMARY OF THE INVENTION

It is an object of the present invention to provide methods for inhibiting FGF signaling in an FGF-responsive cell. More specifically, the present invention relates to methods for inhibiting FGF2-FGFR1 or FGF4-FGFR1 signaling. In one aspect the method for inhibiting FGF signaling comprises contacting an FGF-responsive cell with exogenous Sulf1 in an amount effective to modify endogenous heparan sulfate, thereby inhibiting FGF signaling. In another aspect, the method for inhibiting FGF signaling comprises contacting an FGF-responsive cell with an exogenous Sulf1-modified glycosaminoglycan compound, the exogenous Sulf1-modified glycosaminoglycan compound being characterized by the ability to reduce binding of FGF2 or FGF4 to FGFR1. In these methods, desulfation of cell surface and/or exogenously added glycosaminoglycans prevents FGF-2 and FGF-4 binding to FGFR1 and, in turn, inhibits FGFR1 activation in desired cell.

In one embodiment, cells are to be contacted directly with exogenous Sulf1 to inhibit FGF signaling. Contact of an FGF-responsive cell with Sulf1 enzymatically modifies the 6-O sulfation of cell surface heparan sulfate, and in doing so, inhibits FGF signaling. Contact of the cell with exogenous Sulf1 prevents FGF2-heparan sulfate-FGFR1, or FGF4-heparan sulfate-FGFR1, ternary complex formation. Prevention of said ternary complex formation prevents FGFR1 dimerization and subsequent FGFR1 activation.

In another embodiment, Sulf1 activity may be used indirectly to achieve inhibition of FGF signaling in an FGF-responsive cell. Contact of an FGF-responsive cell with a sulfated glycosaminoglycan compound, such as heparin, which itself has been modified by Sulf1, may be used to inhibit FGF signaling. In this method, the exogenous Sulf1-modified compound is characterized by the ability to reduce binding of an FGF ligand to FGFR. Contact of the cell with the exogenous Sulf1-modified compound prevents FGF2- heparan sulfate-FGFR1, or FGF4-heparan sulfate-FGFR1, ternary complex formation. Prevention of said ternary complex formation prevents FGFR1 dimerization and subsequent FGFR1 activation.

Methods of the invention are to be used for modulating cellular responses to FGFR1 activation. Methods disclosed herein for inhibiting FGF signaling may be used to alter proliferation, differentiation, and migration events in normal and/or abnormal cells contacted with exogenous Sulf1 and/or an exogenous Sulf1-modified glycosaminoglycan compound. Such cells may comprise stem cells or cancerous cells. Wherein the cells are cancerous cells, contact of an FGF-responsive cell with exogenous Sulf1 and/or a Sulf1-modified compound inhibits FGF signaling, and, in turn, inhibits cellular proliferation, cellular migration, and angiogenesis. Wherein the cells are stem cells, contact of an FGF-responsive cell with exogenous Sulf1 and or/Sulf1-modified compounds are to be used to inhibit FGF signaling, and, in turn, suppress mesoderm formation and thereafter redirect cellular differentiation to ectoderm.

It is a further object of the invention to provide compositions for use in conjunction with methods of the present invention. Compositions of exogenous Sulf1-modified glycosaminoglycan compounds are provided, and include exogenous heparin, heparan sulfate, and heparin/heparan sulfate mixtures. An in vitro method for the production of exogenous Sulf1-modified glycosaminoglycan compounds is also herein provided.

DETAILED DESCRIPTION OF THE INVENTION

Figure 1:
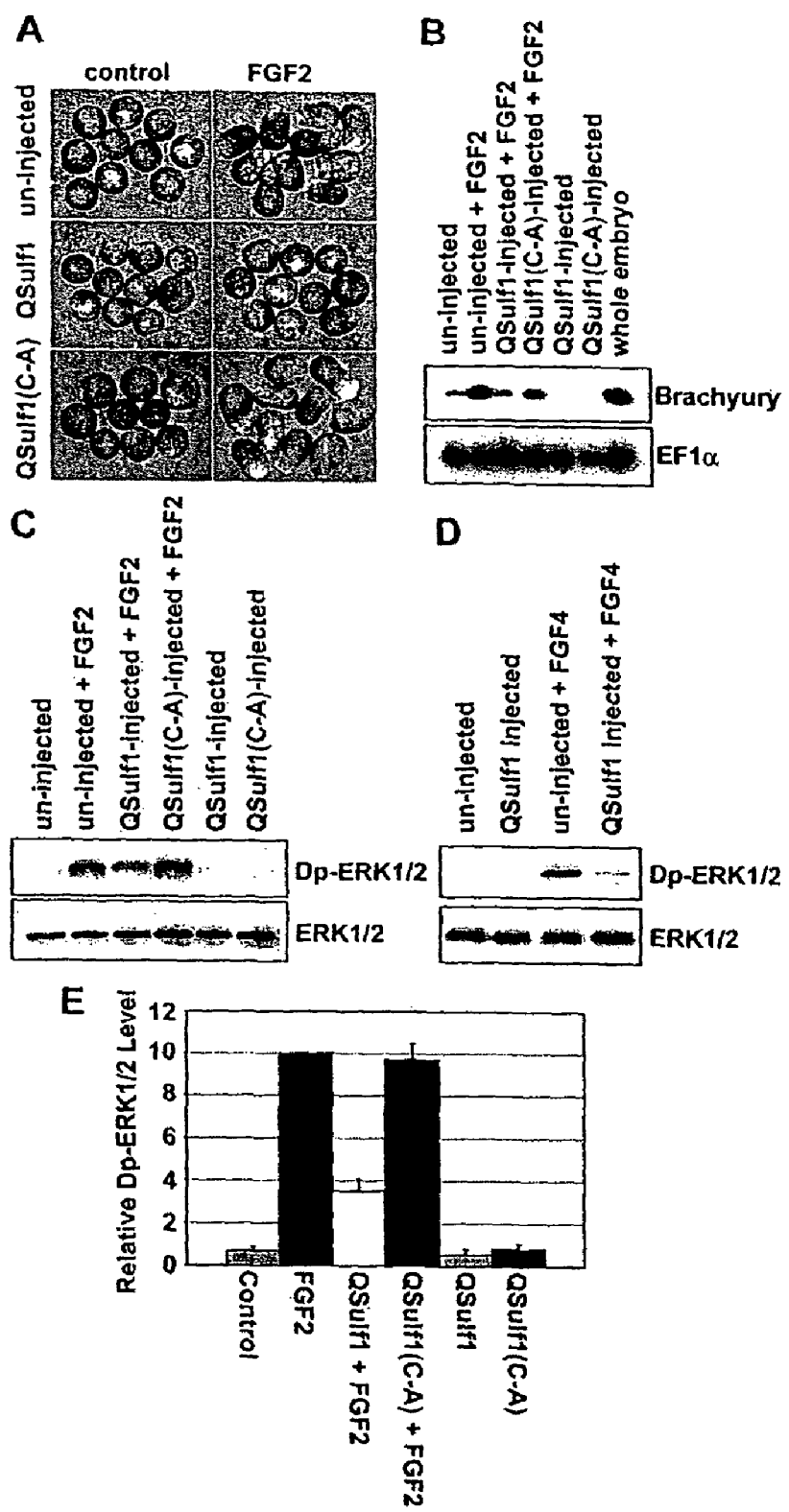
FIG. 1 represents data demonstrating QSulf1 suppression of FGF-induced mesoderm induction in *Xenopus* animal cap assays. *Xenopus* embryos were injected with wild type QSulf1 or mutant QSulf1 (C-A) mRNAs (750 pg) at the one-cell stage. Animal caps were dissected at stage 8-9 and cultured to assess mesoderm induction and ERK1/2 activation. (A) In the absence of FGF2, animal cap explants form epidermis and assume a spherical shape, but caps elongate and form mesodermal tissues when induced with FGF. Expression of wild type QSulf1, but not catalytically inactive QSulf1 (C-A) blocks FGF2-induced animal cap elongation. (B) Animal caps were cultured until stage 11 before isolation of RNA to assess gene expression by RT-PCR assay. QSulf1 suppresses mesodermal gene expression (Brachyury) induced by FGF2 (30 ng/ml), while catalytically inactive QSulf1 (C-A) does not block FGF2-induced Brachyury expression. EF1α was used as a gel loading control and whole embryo RNA as a positive control for expression of mesoderm genes. (C, D) For assays of ERK1/2 phosphorylation, animal caps were cultured for one hour in the presence or absence of FGF2 or FGF4 (30 ng/ml), and protein extracts were prepared for Western blot analysis using antibodies to detect di-phosphorylated ERK1/2 (Dp-ERK1/2) and total ERK1/2 proteins. Erk1/2 phosphorylation is widely applied assay for FGF signaling (Lai et al., *J. Biol. Chem.* 278, 23107-23117 (2003); Pownall et al., *Developmental Biology* 256, 89-99 (2003)). Total ERK1/2 levels were used as a standard to monitor gel loading. FGF2-induced Dp-ERK1/2 phosphorylation is suppressed by QSulf1, but not by enzymatically inactive QSulf1(C-A) (C). QSulf1 also suppressed FGF4-induced Dp-ERK1/2 activation (D). E. Phosphorylation of ERK1/2 shown in panel C was quantified and presented as the mean with standard deviation from 4 independent experiments. The relative Dp-ERK1/2 levels were calculated by measuring the ratios of Dp-ERK1/2 to total ERK1/2, and then normalizing to a FGF2-induced level that was arbitrarily assigned a value of 10. QSulf1 repression of FGF2-induced Dp-ERK1/2 was statistically significant from FGF2 control ($p<0.001$), whereas QSulf1 (C-A) had no effect on FGF2 signaling activity ($p=0.72$).

The present invention relates, in one aspect, to methods for inhibiting FGF signaling in an FGF-responsive cell. More specifically, the present invention relates to methods for inhibiting FGF signaling by exploiting the enzymatic activity of a previously identified heparan sulfate 6-O endosulfatase, Sulf1. In the present invention, Sulf1 activity is used to enzymatically modify the sulfation of cell surface or exogenous glycosaminoglycan ligands. Desulfation of cell surface and/or exogenously added glycosaminoglycans prevents FGF-2 and FGF-4 binding to FGFR1 and, in turn, inhibits FGFR1 activation in desired cells.

The present invention is based on the discovery that Sulf1 enzymatic activity can suppress FGF signaling in an FGF-responsive cell. As disclosed in the Exemplification section which follows, suppression with respect to FGF2 and FGF4 signaling through FGF1 has been demonstrated. It is an object of the present invention that Sulf1 suppress FGF signaling by modifying the 6-O sulfation of cell surface heparan sulfate and/or exogenously added heparin compounds. It is understood in the art that 6-O sulfation of heparan sulfate chains is required for effecting proper FGF signaling in FGF-responsive cells. Sulfation of glycosaminoglycans in general is known to be required for FGF ligand-receptor interactions and FGF signaling. It is further known in the art that sulfation at the 6-O position of glucosamine residues is specifically required for FGF2-FGFR1 and FGF4-FGFR1 interactions, and that 6-O sulfation is crucial for FGF signaling activity. Sulf1 activity regulates 6-O sulfation, but prior to the present invention the involvement of Sulf1 in controlling FGF signaling was not known. In the present invention, Sulf1 activity is used to enzymatically modify the 6-O sulfation of cell surface heparan sulfate or exogenous heparin compounds in effecting modulation of FGF signaling.

In one embodiment, cells can be contacted directly with exogenous Sulf1 to inhibit FGF signaling. This method comprises contacting an FGF-responsive cell with exogenous Sulf1 enzyme in an amount effective to modify endogenous heparan sulfate, and thereby inhibit FGF signaling in the FGF-responsive cell. In this embodiment, Sulf1 enzymatically modifies the 6-O sulfation of cell surface heparan sulfate, and in doing so, inhibits FGF signaling. In this embodiment, exogenous Sulf1 is characterized by the ability to remove at least a subset of 6-O sulfate groups of the endogenous heparan sulfate. It is an object of the present invention that the exogenous Sulf1 prevent FGF2-heparan sulfate-FGFR1 ternary complex formation. It is another object of the present invention that the exogenous Sulf1 prevent FGF4-heparan sulfate-FGFR1 ternary complex formation. Prevention of FGF2-heparan sulfate-FGFR1 ternary complex formation and prevention of FGF4-heparan sulfate-FGFR1 ternary complex formation prevents FGFR1 dimerization and subsequent FGFR1 activation.

In another embodiment of the present invention, inhibition of FGF signaling can be achieved indirectly by Sulf1. In this embodiment, cells are contacted with a sulfated glycosaminoglycan, such as heparin, which itself has been modified by Sulf1 in vitro. Inhibiting FGF signaling in an FGF-responsive cell comprises contacting the FGF-responsive cell with an exogenous Sulf1-modified heparin compound. It is a requirement of the present invention that the exogenous Sulf1-modified heparin compound possess the ability to reduce binding of an FGF ligand to FGFR. In this embodiment, Sulf1 is used to enzymatically modify the 6-O sulfation of the exogenous heparin compound. In a preferred embodiment, the exogenous Sulf1-modified heparin compound is characterized by the removal of at least a subset of 6-O sulfate groups of the exogenous heparin compound. It is an object of the present invention to contact an FGF-responsive cell with the exogenous Sulf1-modified heparin compound in preventing FGF2-heparan sulfate-FGFR1 ternary complex formation. It is another object of the present invention that the exogenous Sulf1-modified heparin compound prevent FGF4-heparan sulfate-FGFR1 ternary complex formation. Prevention of FGF2-heparan sulfate-FGFR1 ternary complex formation and prevention of FGF4-heparan sulfate-FGFR1 ternary complex formation, in turn, prevents FGFR1 dimerization and subsequent FGFR1 activation.

It is yet another object of the present invention to provide an in vitro method for the production of Sulf1-modified heparin compounds, the Sulf1-modified heparin compound being characterized by its ability to inhibit FGF-heparan sulfate-FGFR ternary complex formation on an FGF-responsive cell. The ternary complex formation inhibited may comprise either FGF2-heparan sulfate-FGFR1 or FGF4-heparan sulfate-FGFR1. Inhibition of FGF2-heparan sulfate-FGFR1 and/or FGF4-heparan sulfate-FGFR1 ternary complex formation prevents FGFR1 dimerization and subsequent FGFR1 activation. The method for producing Sulf1-modified heparin compounds described herein comprises contacting a heparin compound or compounds with Sulf1 in an amount and for a sufficient period of time to effectively remove at least a subset of the heparin 6-O sulfate groups. Typically an incubation of Sulf1 with heparin at 37 for several hours is sufficient to provide Sulf1-modified heparin, the Sulf1-modified heparin being characterized by its ability to inhibit FGF-heparan sulfate-FGFR1 ternary complex formation on an FGF-responsive cell. It is not a requirement that any particular temperature, incubation period, or buffer conditions be utilized in production of Sulf1-modified heparin compounds, only that the Sulf1-modified heparin compounds produced by the contact of Sulf1 with heparin be able to inhibit FGF-heparan sulfate-FGFR1 ternary complex formation. In this embodiment, it is not a requirement that the Sulf1 enzyme directly contact the FGF-responsive cell.

Methods disclosed herein for inhibiting FGF signaling in an FGF-responsive cell can be carried out in vitro. Inhibition of FGF signaling can be effectively achieved in an FGF-responsive cell in tissue culture. FGF signaling is conserved in vertebrates and nonvertebrates, and, as such, methods for inhibiting the same may be carried out in tissue culture cells derived from either vertebrates or nonvertebrates. Examples of vertebrate cell lineages in which FGF signaling is converved include humans and mice. Examples of invertebrate cell lineages in which FGF signaling is conserved include *C. elegans* and *Drosophila*. In vitro, the methods disclosed herein for inhibiting FGF signaling may be used to study FGF signaling or for the development of therapeutics for modifying FGF signaling. The methods disclosed herein are not intended to be limited only for use with cells in culture.

Methods disclosed herein for inhibiting FGF signaling in an FGF-responsive cell can also be carried out in vivo. Inhibition of FGF signaling can be effectively achieved in cells within an animal. Inhibition of FGF signaling in cells within an animal may be achieved wherein the animal is human or non-human. FGF signaling is conserved in vertebrates and nonvertebrates, and, as such, methods for inhibiting the same may be carried out in either vertebrates or nonvertebrates. Examples of vertebrates in which FGF signaling is converved include humans and mice. Examples of invertebrates in which FGF signaling is conserved include *C. elegans* and *Drosophila*. The methods disclosed herein are not intended to be limited only for use with cells in any particular tissue or animal. In vivo, the methods disclosed herein for inhibiting FGF signaling may be used to alter cell fate decisions in a developing or mature animal.

It is an object of the present invention to employ the methods disclosed herein for modulating cellular responses to FGFR1 activation. It is known in the art that activation of FGF signaling is crucial for normal cellular proliferation, differentiation, and migration events to occur during the course of normal animal development. FGF signaling is known in the art to stimulate limb bud formation during vertebrate development and is also known for stimulating proper wound healing and angiogenesis in adult tissues. Hyperactive FGFRs have been implicated in a number of disease states. The effects of FGFR activation on cellular proliferation, differentiation, migration, and angiogenesis have implicated the involvement of FGFR in cancer. A number of genetic disorders have been associated with FGFR mutations, including skeletal disorders such as achondroplasia (dwarfism), hypochondroplasia, and thanatophoric dysplasia, disorders which are presumed to occur because of premature closure of skull sutures or because of the premature termination of long bone growth. These mutations have been suggested to arise from overactive FGFRs which result in overactive cellular proliferation, differentiation, and migration of progenitor cells.

Methods disclosed herein for inhibiting FGF signaling may be used to alter proliferation, differentiation, and migration events in normal and/or abnormal cells contacted with exogenous Sulf1 and/or exogenous Sulf1-modified heparin. Such cells may comprise stem cells and cancerous cells. In cancerous cells, contacting an FGF-responsive cell with exogenous Sulf1 and or/Sulf1-modified heparin compounds would inhibit FGF signaling, and, in turn, inhibit cellular proliferation, cellular migration, and angiogenesis. Inhibition of FGF-induced cellular proliferation in cancerous cells would result in an inhibition of tumor cell growth. Inhibition of FGF-induced cellular migration in cancerous cells would result in an inhibition of metastatic events. Finally, inhibition of FGF-induced angiogenesis in cancerous cells would inhibit the formation of blood vessels, thereby cutting off the food supply to the tumor.

The present disclosure provides the first in vivo evidence that Sulf1 can regulate FGF-controlled developmental processes in embryos. It is an object of the instant invention to utilize methods for inhibiting FGF signaling in an FGF-responsive cell for altering FGF-controlled developmental processes in embryos or progenitor cells. In a preferred embodiment, contacting an FGF-responsive cell with exogenous Sulf1 and/or Sulf1-modified heparin compounds in an amount effective to modify endogenous heparan sulfate inhibits FGF signaling. Contacting FGF-responsive cells with exogenous QSulf1 was shown to suppress FGF2 signaling in the FGF-responsive progenitor cells, resulting in the subsequent suppression of mesoderm formation. The methods of the present invention can thus be utilized in preventing the differentiation of progenitor cells from forming muscle, blood, and bone cells in addition to cells that give rise to organs of the reproductive and excretory systems. In preventing the induction of mesoderm, the progenitor cells can instead be redirected to form ectoderm. Redirecting cellular differentiation to ectoderm provides for the formation of epidermal and nervous system tissue. Inhibition of FGF signaling in FGF-responsive progenitor cells results in promoting stem cell production. Methods disclosed herein for inhibiting FGF signaling in FGF-responsive cells can therefore be useful in stem cell based therapies for tissue and organ regeneration.

It is a further object of the present invention to provide methods for inhibiting components of the FGF signaling cascade which lie downstream of FGFR. FGFRs are known in the art to be part of a complex signal transduction cascade. FGFRs, when activated, activate downstream intracellular signaling components, which include Ras, Raf, MEK, MAPK, and ERK. Binding of FGF to FGFR dimerizes the receptor, thereby activating its receptor tyrosine kinase activity. FGF receptor tyrosine kinase activity stimulates a cascade of phosphorylation intracellularly which includes phosphorylation and subsequent activation of Ras, Raf, MEK, MAPK, and ERK as well as further downstream targets. Methods disclosed herein for inhibiting FGF signaling in an FGF-responsive cell comprising contacting the FGF-responsive cell with exogenous Sulf1 or Sulf1-modified heparin would also be effective in inhibiting these signaling events downstream of FGFR1.

Also provided herein is a composition for use in some of the methods disclosed herein. A composition comprising exogenous Sulf1-modified heparin compounds are provided, the composition having the ability to reduce binding of FGF2 or FGF4 to FGFR1 in the method comprising contacting an FGF-responsive cell with the exogenous Sulf1-modified heparin compound, wherein the reduction in binding of FGF2 or FGF4 to FGFR1 results in an inhibition of FGF signaling in the FGF-responsive cell. Examples of exogenous Sulf1-modified heparin compounds include heparin, heparan sulfate, and heparin/heparan sulfate mixtures. The size of the individual heparin and heparan sulfate chains can vary, but relatively short chains are preferable. The exogenous Sulf1-modified heparin compounds may be used to inhibit cellular proliferation, differentiation, and migration of cells in culture or in vivo. The exogenous Sulf1-modified heparin compounds may also be used to inhibit angiogenesis or mesoderm formation in tissues. The exogenous Sulf1-modified heparin compounds may further be used to promote stem cell production or for the treatment of cancer or other disease states due to defects in heparin-dependent signaling pathways.

The exogenous Sulf1-modified heparin compounds provided herein are particularly attractive therapeutic compounds, as heparin-based compounds and methods for their delivery are known in the art. Heparin compounds are well-characterized, relatively safe drugs, and heparin-based therapies are well established in the art. Heparin has long been widely used as an anticoagulant for treating ischemia. Heparin compounds have been proven to be stable and nontoxic when introduced in vivo.

In the methods of the present invention, exogenous Sulf1 or exogenous Sulf1-modified heparin compounds would be administered in a physiologically acceptable carrier in a therapeutically effective amount. Said compound or compounds may be administered alone or in combination with other therapies and may be delivered intravenously, subcutaneously, or orally to an animal. Administration may be systemic, although local administration is preferable.

An FGF-responsive cell may express exogenous Sulf1 from an introduced exogenous construct harboring an expressible Sulf1 cDNA (Gen Bank Accession No. BC012997). FGF-responsive cells may be transformed with the expressible Sulf1 cDNA construct. In animals, the construct may be delivered by methods of gene therapy which are known in the art. Alternatively, Sulf1 RNA or protein may be delivered to cells by injection or other delivery means already known in the art.

Because the therapeutic targets of the present invention are extracellular, delivery of Sulf1 enzyme or Sulf1-modified heparin compound need only be extracellular. It is not a requirement of the present invention that exogenous Sulf1 or exogenous Sulf1-modified heparin compounds be delivered intracellularly. In the methods of the present invention, the pharmaceutical challenge of intracellular delivery, therefore, is overcome. Exogenous Sulf1 enzyme or exogenous Sulf1-modified heparin compounds can be delivered to the extracellular surface of FGF-responsive cells in which inhibition of FGF signaling is desired.

In an FGF-responsive cell that expresses exogenous Sulf1 from an exogenous construct harboring an expressible Sulf1 cDNA, active Sulf1 is expressed intracellularly, secreted extracellularly, and active on the cell surface. Desulfation of cell surface heparan sulfate is known to occur on the cell surface of living cells. Cells expressing active Sulf1, when plated on tissue culture plates coated with labeled heparan sulfate in an inert extracellular matrix, effectively release sulfate from the surface of the plates. In comparison, cells expressing inactive Sulf1 are unable to release sulfate from the surface of the plates, demonstrating that Sulf1 is enzymatically active and functional on the surface of the cell. Furthermore, cells expressing active Sulf1 that has been modified to prevent its release from the Golgi cannot release sulfate from tissue culture plates coated with labeled heparan sulfate in an inert extracellular matrix.

Exemplification

A. Materials and Methods i) Plasmids, mRNAs, and recombinant proteins. QSulf1 cDNA encoding full-length QSulf1 protein was subcloned into pAG-myc and pCS2 vectors for mammalian cell expression and in vitro synthesis of QSulf1 mRNA, respectively. pCS2-XFGFR1K562E plasmid was kindly provided by Dr. Robert Friesel (Neilson & Friesel, *J. of Biol. Chem.* 271, 25049-57 (1996)). A construct encoding soluble FGFR1 receptor with its extracellular domain tagged with alkaline phosphatase (pFGFR1c-AP) was a gift from Dr. Alan Rapraeger (Allen et al., *J. Cell Biol.* 155, 845-58 (2001)). The drug-inducible iFGFR1 was activated with AP20187 (provided by Ariad) (Pownall et al., *Developmental Biology* 256, 89-99 (2003)). Human recombinant FGF2 protein was purchased from Sigma, and *Xenopus* FGF4 (eFGF) was produced using the expression construct, pET-XeFGFi (Isaacs et al., *Development* 114, 711-20 (1992)). QSulf1, QSulf1 (C-A) mutant, FGFR1K562E, and iFGFR1 mRNAs were synthesized using the mMessage kit (Ambion) and quantified using a spectrophotometer. Active QSulf1 and catalytically inactive QSulf1 (C-A) proteins were purified from 293T cells stably transfected with pAG-QSulf1 and pAG-QSulf1 (C-A), as described (Ai et al., *Journal of Cell Biology* 162, 341-51 (2003)).

ii) Animal cap assays. *Xenopus leavis* embryos were obtained following standard protocols (Slack et al., *Nature* 326, 197-200 (1987); Yao & Kessler, *Methods in Molecular Biology* 137, 169-178 (2000)). Embryos were injected in the animal pole at the one-cell stage with mRNAs as described in the Brief Description of the Drawings. Injected embryos were cultured in 0.1×MMR (Yao & Kessler, Methods in Molecular Biology 137, 169-178 (2000)) until stage 8-9 when animal caps were isolated. Animal caps were cultured in 0.5×MMR plus gelatin (100 ng/ml), recombinant proteins, AP20187, and heparin as specified in the Brief Description of the Drawings. Ten animal caps were collected for each experimental group. Data shown are representative of at least three independent experiments. The use of *Xenopus* and quail embryos was approved by the IACUC committee of the University of Pennsylvania.

iii) Western blotting analysis for ERK1/2. Animal caps were lysed in 15 µl of buffer containing 80 mM beta-glycerophosphate, 20 mM EGTA, 1 mM DTT, 15 mM MgCl$_2$, 20 mM Hepes pH 7.5, and Complete® cocktail of protease inhibitors (Roche). Samples were heated at 75° C. for 5 minutes after adding protein sample buffer (4× concentration, BioRad) to the supernatants obtained by centrifuging at 14,000 g. For diphosphorylated ERK1/2 (Dp-ERK1/2) and total ERK1/2 detection, 14 µl and 2 µl (plus 10 µl of 1× loading buffer), respectively, of the samples were loaded onto separate 10% SDS-PAGE minigels (BioRad). TBST (10 mM Tris pH 7.5, 150 mM NaCl, 0.1% Tween-20) plus 5% non-fat-milk was used for Hybond-ECL nitrocellulose membrane (Amersham) blocking and antibody incubations. Membranes were incubated with total ERK1/2 antibody (1:4000, Sigma) or Dp-ERK1/2 antibody (1:2000, Sigma) for one hour, washed with TBST in four 5 minutes changes, incubated with peroxidase labeled secondary antibodies (Amersham, 1:2000 and 1:4000 for Dp-ERK1/2 and total ERK1/2 detection, respectively), and washed. Signals were developed using the ECL-plus kit (Amersham), captured on X-ray films, scanned with Storm Imager, and quantified with ImageQuant software (Molecular Dynamics).

iv) RT-PCR assays. Animal caps were cultured until stage 11 for gene expression analysis. Total RNA was purified from animal caps and embryos using RNAqueous™ kit (Ambion) and quantified by spectrophotometer. Protocols for cDNA synthesis, PCR primers for EF1α, Brachyury, MyoD, PCR conditions, and gel electrophoresis were performed as described (Engleka et al., *Developmental Biology* 237, 159-72 (2001)). Data shown are representative of 5 independent assays.

v) FGF2-heparin beads binding assay. Heparin conjugated to acrylic beads (Sigma) was digested with QSulf1 or QSulf1 (C-A) mutant protein at 37° C. overnight on a shaker (Ai et al., *Journal of Cell Biology* 162, 341-51 (2003)). Heparin-beads were collected by centrifuging and washing with Hank's balanced saline solution (HBSS, Invitrogen), then aliquoted in 50 μl volumes containing 20 μl beads for binding assays. Treated heparin-beads were incubated with varying amounts of FGF2 at room temperature for 30 minutes and then washed. FGF bound to heparin-beads was analyzed by Western blotting. Data shown are representative of three independent experiments.

vi) In vitro FGF2 binding to FGFR1c-AP. FGFR1c-AP protein was obtained from the conditioned medium of 293T cells transfected with pFGFR1c-AP, 48 hours after switching to serum-free DMEM/F12 (InVitrogen). Protein in conditioned medium was quantified by colorimetric dye concentrate assay (BioRad). The purification of QSulf1 and enzymatic digestion of heparin were as described (Ai et al., *Journal of Cell Biology* 162, 341-51 (2003)). The binding assay mixtures (200 μl total volume containing 10 ng FGF2, 10 ng FGFR1c-AP, and varying amounts of heparin pretreated with either QSulf1 or QSulf1 (C-A) in HBSS) were incubated for 30 minutes at room temperature. Complexes were immunoprecipitated after 2 hr incubation with 10 μl of a slurry of anti-AP antibody coupled to agarose beads (Sigma). FGF2 bound to FGFR1c-AP was resolved by 10% SDS-PAGE, and detected by Western blotting, and quantitated using ImageQuant. Dilution of anti-FGF2 antibody was 1:2000 (Sigma).

vii) Chorioallantonic membrane angiogenesis assay. Fertilized chick eggs were incubated in a humidified 38° C. oven for 10 days. Filter papers (0.25 cm$^2$) soaked in 10 μl of PBS containing 20 ng FGF2 with control heparin or QSulf-1-digested heparin (200 ng) were applied to an avascular area on the chorioallantonic membrane exposed through a window in the shell. The eggs were sealed with tape and incubated for three additional days. The chorioallantonic membrane was then excised adjacent to the filters, fixed and examined under the microscope to count numbers of blood vessel branches on each filter (Lundin et al., *J. of Biol. Chem.* 275, 24653-60 (2000)). Angiogenesis was scored from 1 (low) to 4 (high) according to Friedlander et al. (Friedlander et al., *Science* 270, 1500-02 (1995)).

Figure 2:
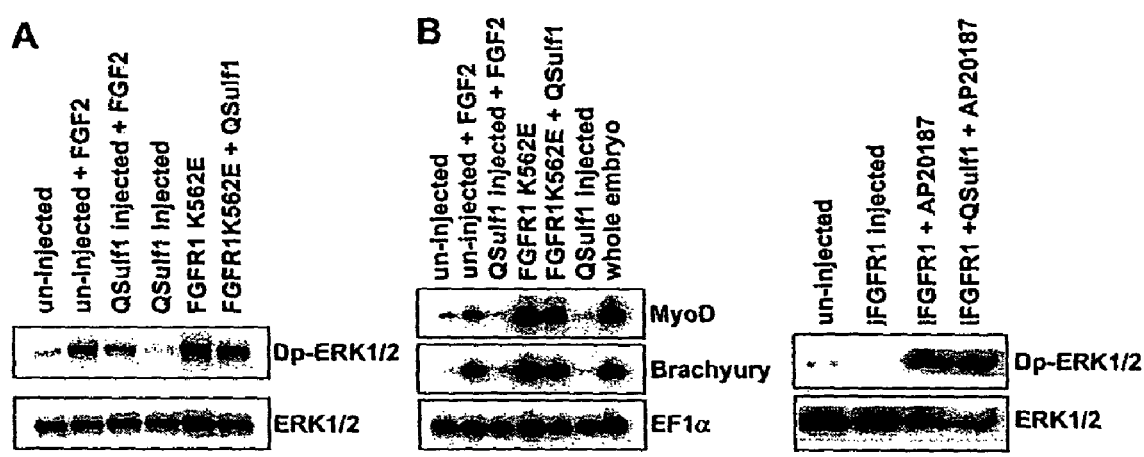
FIG. 2 represents data demonstrating that constitutively activated FGFR1 receptors bypass QSulf1 inhibition of FGF2 and FGF4 signaling. FGFR1K562E is a FGFR1 receptor with an intracellular domain mutation conferring constitutive activity, independent of FGF ligand binding (A, B). iFGFR1 is a membrane-docked FGFR1 receptor with a deleted extracellular domain and an added intracellular domain to promote receptor dimerization and inducible activation in response to addition of the drug AP 20187 (C). QSulf1 mRNA (2 ng) was injected alone or co-injected with FGFR1K562E mRNA (100 pg) or iFGFR1 mRNA (20 pg) into one-cell stage *Xenopus* embryos. Animal caps were dissected at stage 8-9 and cultured for Western blot analysis of phosphorylated ERK1/2 (Dp-ERK1/2) and total ERK1/2 (ERK1/2) (A, C), and by RT-PCR analysis to assay mesodermal gene expression (B). (A) Protein extracts were assayed one hour after FGF2 treatment by Western blot analysis of Dp-ERK1/2. QSulf1 suppresses FGF2 (30 ng/ml), but not FGFR1K562E activation of Dp-ERK1/2. (B) QSulf1 suppresses FGF2, but not FGFR1K562E induction of mesodermal markers, Brachyury and MyoD. Whole embryo samples provided a positive control for mesodermal gene expression. (C) AP20187 (1.25 μM) activation of iFGFR1 receptor induces Dp-ERK1/2 activation in the presence of QSulf1.

B. Results and Discussion i) QSulf1 suppresses FGF2 signaling and mesoderm induction. The *Xenopus* animal cap assay was employed to study QSulf1 activity in FGF signaling. Explants of the animal pole region of the *Xenopus* blastula will form ectodermal derivatives when untreated (Yao & Kessler, *Methods in Molecular Biology* 137, 169-178 (2000)). Treatment of explants with exogenous FGF protein results in elongation and mesodermal differentiation (Slack et al., *Nature* 326, 197-200 (1987)), providing a convenient FGF signaling assay system. QSulf1 and a catalytically inactive mutant form, QSulf1 (C-A) (Dhoot et al., *Science* 293, 1663-6 (2001)), were over expressed in animal caps by injecting in vitro synthesized mRNAs into *Xenopus* embryos at the one-cell stage, followed by isolation of animal pole explants at blastula stage. Over expression of QSulf1 or QSulf1 (C-A) alone did not induce morphological changes or expression of mesodermal marker genes. However, QSulf1 suppressed both FGF2-induced tissue elongation (FIG. 1A) and mesodermal differentiation, as assayed by expression of the mesodermal gene Brachyury (FIG. 1B). The enzymatically-inactive QSulf1(C-A) did not block FGF2-induced tissue elongation and slightly inhibited Brachyury expression. QSulf1 expression also strongly suppressed the phosphorylation of ERK1/2, which are direct targets of the FGF2 signaling pathway (FIG. 1C, 1E). By contrast, QSulf1 (C-A) had no effect on the induction of phosphorylated ERK1/2 (FIG. 1C, 1E), establishing that QSulf1 directly regulates FGF signaling though its enzymatic activity. The slight inhibitory activity of QSulf1 (C-A) on Brachyury expression, therefore, likely reflects a non-specific response. QSulf1 is similarly active in the inhibition of mesoderm formation induced by FGF4 (eFGF), the FGF isoform normally active in the *Xenopus* embryo (FIG. 1D) (Slack et al., *Nature* 326, 197-200 (1987)). These data, therefore, establish that QSulf1 functions enzymatically to inhibit FGF-induced mesodermal differentiation, through a mechanism that operates upstream of ERK1/2 phosphorylation. Interestingly, the inhibitory activity of QSulf1 on FGF signaling contrasts with its positive regulatory activity on Wnt signaling (Ai et al., *Journal of Cell Biology* 162, 341-51 (2003)), indicating that QSulf1 has dual regulatory functions and that HS-mediated FGF and Wnt signaling have different requirements for 6-O sulfation of HS.

ii) QSulf1 functions upstream of FGFR1 receptor to modify extracellular HS. A set of experiments was carried out which focused on determining whether QSulf1 acts upstream of the FGFR1 receptor to inhibit FGF signaling, as predicted from its activity in the desulfation of extracellular HS (Ai et al., *Journal of Cell Biology* 162, 341-51 (2003)). For these studies, constitutively active mutant forms of FGFR1 were co-expressed with QSulf1 in animal caps, which were tested for the ability to respond to FGF signaling, as assayed by mesoderm induction and ERK1/2 phosphorylation. Two different mutant forms of FGFR1 receptor were used for these studies. In one case, FGFR1K562E was used, which has a mutation in its intracellular tyrosine kinase domain that constitutively activates tyrosine kinase activity independent of its normal requirement for HS-mediated receptor dimerization (Neilson & Friesel, *J. of Biol. Chem.* 271, 25049-57 (1996)). A second FGFR1 mutant (iFGFR1) lacks the extracellular ligand binding domain, but has a membrane targeting, amino-terminal myristilation sequence and two mutated FKBP12 domains that bind the synthetic drug AP20187 to promote receptor dimerization and receptor activation in response to drug addition (Pownall et al., *Developmental Biology* 256, 89-99 (2003)). It was reasoned that these constitutively activated FGFR1 receptors would be resistant to QSulf1 inhibition of FGF signaling if QSulf1 functions to modify cell surface HS required for receptor dimerization. FGFR1K562E or iFGFR1 were both insensitive to the inhibitory activity of QSulf1 for FGF signaling activation, as shown by high level of Dp-ERK1/2 activation (FIG. 2A, C) and induction of mesodermal genes (FIG. 2B).

Figure 3:
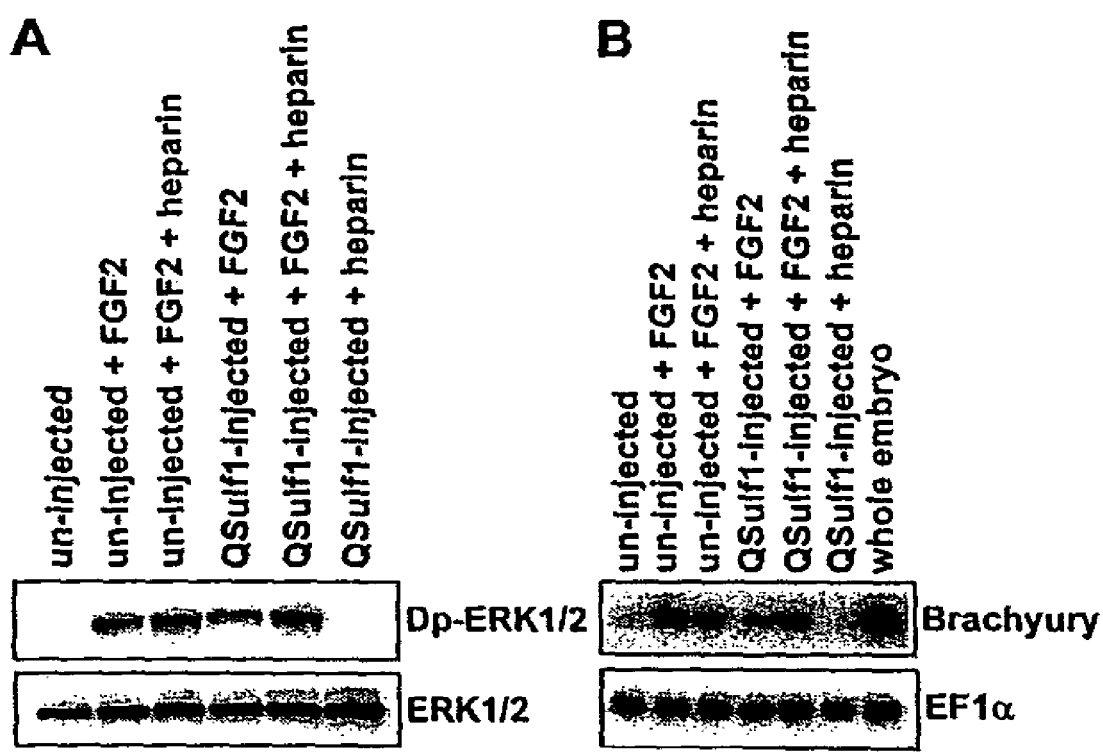
FIG. 3 represents data demonstrating that exogenous heparin rescues the suppression of FGF2 signaling by QSulf1. QSulf1 mRNA was injected into one-cell stage *Xenopus* embryos (2 ng). Animal caps were dissected at stage 8-9 and cultured. Sulfated heparin was added to the culture media at a concentration of 150 ng/ml. (A) Animal caps were collected after one hour of FGF2 treatment. QSulf1 suppressed the ERK1/2 activation induced by FGF2 protein (30 ng/ml) and this suppression was rescued by exogenous heparin. Total ERK1/2 was assayed as a gel loading control. (B) Animal caps were cultured until stage 11 to assess gene expression. QSulf1 suppression of mesodermal gene (Brachyury) expression was rescued by exogenous heparin. The constitutively expressed EF1α served as a gel loading control, and RNA prepared from whole embryos served as a positive control for the assay of mesoderm gene expression.
Figure 4:
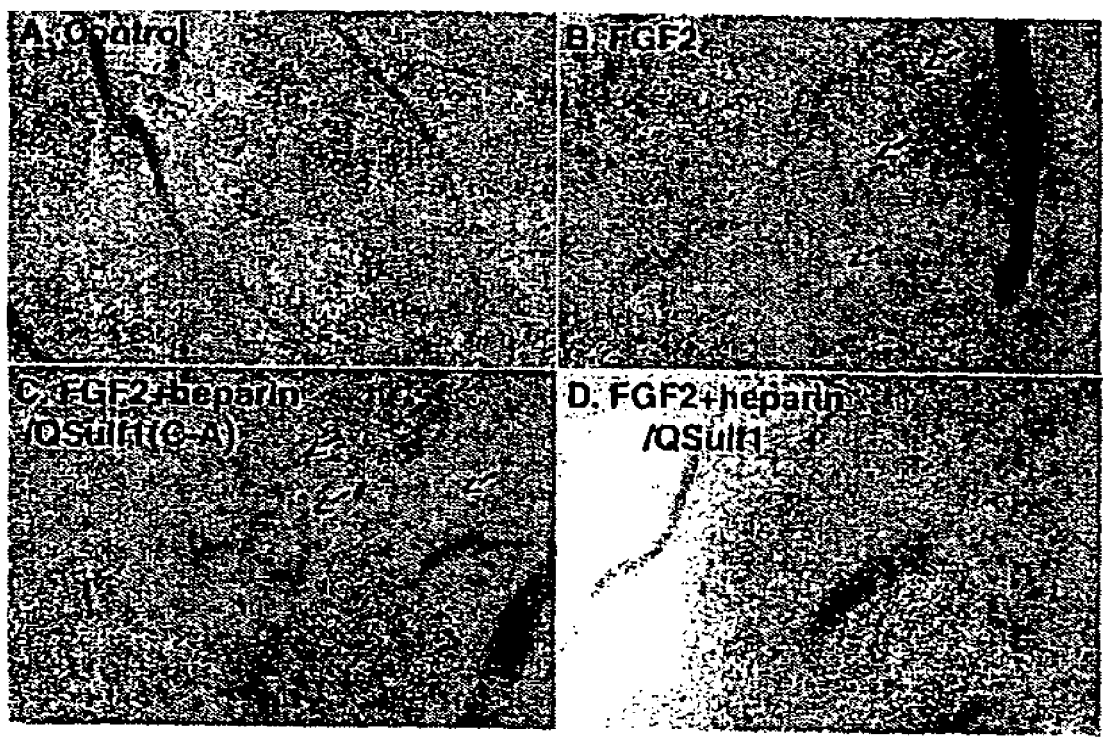
FIG. 4 represents data demonstrating that QSulf1-treated heparin suppresses FGF2-induced angiogenesis. Filters soaked with FGF2, with or without heparin, were applied to the chorioallantoic membrane of day 10 chicken embryos. Blood vessel formation on the membrane was analyzed after 3 days. More than 12 filters from three independent experiments were examined for each experimental group. (A) Application of control PBS filter did not induce formation of blood vessel branches in 9 out of 13 samples. (B) Application of FGF2 (20 ng) filter induced formation of blood vessel branches in 8 out of 12 samples. (C) Application of filter containing FGF2 and QSulf1 (C-A)-treated heparin (200 ng) did not affect formation of blood vessel branching induced by FGF2 in 12 out of 14 samples. (D) Application of filter containing FGF2 and QSulf1-treated heparin (200 ng) suppressed FGF2 induction of blood vessel branches in 9 out of 15 samples. Arrows indicate formation of blood vessel branches.

To test whether QSulf1 functions by modifying the sulfation of extracellular HS, experiments were conducted to determine whether exogenously added heparin could rescue QSulf1 inhibition of FGF signaling in the animal cap assay. QSulf1-injected animal caps were cultured in the presence or absence of heparin, which is a highly sulfated HS glycosaminoglycan substrate for Sulf1 (Morimoto-Tomita et al., *Journal of Biological Chemistry* 277, 49175-85 (2002); Ai et al., *Journal of Cell Biology* 162, 341-51 (2003)) and capable of rescuing FGF2 signaling in cells deficient in HS biosynthesis (Ornitz et al., *Mol. Cell Biol.* 12, 240-247 (1992); Lundin et al., *J. of Biol. Chem.* 275, 24653-60 (2000)). At concentrations (150-250 ng/ml) that rescue FGF2 signaling in cultured cells (Fannon et al., *Biochemistry* 39, 1434-45 (2000)), exogenous heparin fully rescued QSulf1 inhibition of FGF2-mediated ERK1/2 activation and mesoderm induction (FIG. 3). Sulf1 also blocks Erk1/2 activation in response to FGF2 and heparin-dependent EGF, but not in response to activation by heparin-independent EGF in cultured ovarian cell lines (Lai et al., *J. Biol. Chem.* 278, 23107-23117 (2003)), further supporting the conclusion that Sulf1 enzymatically modifies the sulfation of extracellular HS specifically for HS-dependent signaling. Notably, uninjected animal caps treated with soluble heparin in the presence or absence of FGF2 are not stimulated further in FGF signaling, indicating that HS on the cell surface of embryonic animal cap is present in excess to control FGFR1 receptor activation and FGF signal transduction.

iii) QSulf1-modified heparin inhibits FGF2-induced angiogenesis. As exogenous heparin rescues FGF signaling in QSulf1-expressing animal cap cells, experiments were carried out to test whether QSulf1-modified heparin can block FGF signaling. For these studies, FGF2 signaling in the chorioallantonic membrane angiogenesis system was examined, providing a sensitive and quantitative in vivo assay for FGF induction, as monitored by blood vessel branching (Lundin et al., *J. of Biol. Chem.* 275, 24653-60 (2000)) and subsequently scored from PBS control 1 (low level of angiogenesis) to 4 (FGF2 induced level of angiogenesis) (Friedlander et al., *Science* 270, 1500-02 (1995)). Control chorioallantoic membranes treated with PBS form blood vessels with were scored as 1 (Table 1, FIG. 4A), whereas membranes treated with FGF2 form vessels with extensive branching and scored as 2.9 on a scale of 14 (FIG. 4B), where a score of 1 equaled 0-2 branches per membrane and a score of 4 equaled 25 branches per membrane. FGF-induced blood vessel branching is nearly completely blocked by the addition of exogenous heparin that had been enzymatically desulfated by QSulf1 scored as 1.1) while inactive QSulf1 (C-A) enzyme has no blocking activity and scored as 2.9 (compare FIGS. 4C& D). Therefore, QSulf1-modified heparin is a potent angiogenesis inhibitor.

TABLE 1

QSulf1 6-O desulfated heparin inhibits FGF2-induced angiogenesis on chick chorioallantonic membrane.

| Treatment | Number of embryos score | Angiogenesis |
|---|---|---|
| PBS | 14 | 1 |
| FGF2 (25 ng) | 15 | 2.9 +/− 0.5 |
| FGF2 + heparin/ QSulf1 (C-A) | 15 | 2.5 +/− 0.7 |
| FGF2 + heparin/ QSulf1 | 14 | 1.1 +/− 0.5 |

Angiogenesis was scored from 1 (low, PBS) to 4 (high) according to Friedlander et al., Science 270, 1500-02 (1995). Data represented are mean and standard deviation of at least 14 embryos from each treatment.

iv) QSulf1-modified heparin disrupts FGF2-FGFR1 complex formation. To investigate the mechanisms by which QSulf1 activity modifies HS to block FGF signaling, experiments were carried out to determine whether QSulf1 alters the ability of heparin to bind to FGF2. Heparin conjugated to acrylic beads was enzymatically treated with QSulf1 or catalytically inactive QSulf1 (C-A) and then incubated together with an excess of FGF2 protein to assay binding. Beads with bound FGF2 were then washed and bound FGF was quantified using Western blotting. These assays revealed that FGF2 binds equally well to QSulf1-treated heparin and QSulf1 (C-A)-treated heparin (FIG. 5A), establishing that QSulf1 treatment does not reduce FGF2 binding to HS. This is consistent with previous findings that FGF2 binding to heparin requires 2-0, but not 6-O sulfates (Schlessinger et al., *Molecular Cell* 6, 743-50 (2000); Lundin et al., *J. of Biol. Chem.* 275, 24653-60 (2000); Pye et al., *J. Biol. Chem.* 273, 22936-42 (1998)), which include the substrates for QSulf1 (Morimoto-Tomita et al., *Journal of Biological Chemistry* 277, 49175-85 (2002); Ai et al., *Journal of Cell Biology* 162, 341-51 (2003)).

Figure 5:
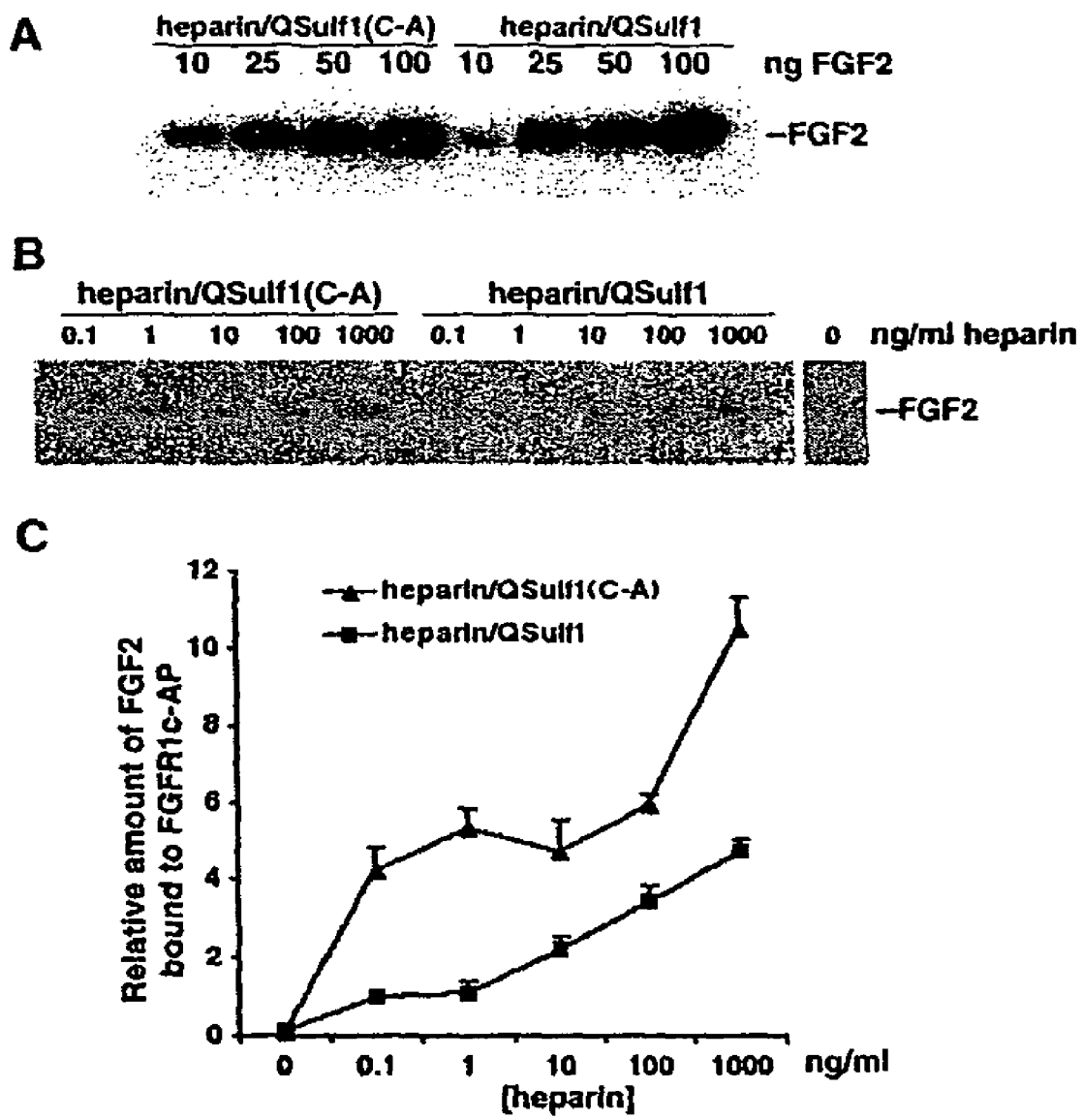
FIG. 5 represents data demonstrating that QSulf1-treated heparin reduces the binding of FGF2 to FGFR1, but not to heparin. (A) QSulf1 does not affect the binding of FGF2 to heparin. Heparin beads pretreated with QSulf1 or QSulf1 (C-A) mutant protein were incubated with the indicated amount of FGF2. The heparin-bound FGF2 was analyzed by Western blotting. No significant difference was detected in FGF2 binding to QSulf1- and QSulf1(C-A)-treated heparin. (B) QSulf1 treatment of heparin reduces the formation of a FGF2-heparin-FGFR1 complex. QSulf1- or QSulf1 (C-A)-treated soluble heparin at the indicated concentrations was incubated with FGF2 (10 ng/ml) and FGFR1c-AP (10 ng/ml). FGFR1c-AP was immunoprecipitated with an anti-AP antibody conjugated to agarose beads and bound FGF2 was detected by Western blotting. (C) Quantification of FGF2 bound to FGFR1c-AP in the presence of QSulf1- or QSulf1 (C-A)-treated heparin. The binding of FGF2 to FGFR1c-AP in the presence of QSulf1-treated heparin was reduced 2-5 fold compared with the binding in the presence of QSulf1(C-A)-treated heparin.

It was then determined whether QSulf1 disrupts the ability of heparin to form FGF2-heparin-FGFR ternary complexes. Heparin-mediated FGF2 ligand-receptor binding was assayed by using a soluble FGFR1c containing the extracellular domain of FGFR1 fused to an AP tag (Allen et al., *J. Cell Biol.* 155, 845-58 (2001)). FGF2 and FGFR1c were incubated with increasing concentrations of QSulf1 or QSulf1 (C-A) treated heparin (0-1000 ng/ml) to allow FGF2-heparin-FGFR ternary complex formation. The complex was then immunoprecipitated with anti-AP antibody. Only a low level of FGF2 was bound to FGFR1c-AP in the absence of heparin (FIG. 5B-C). Heparin treated with control QSulf1 (C-A) enzyme promotes binding of FGF2 to FGFR1c, whereas QSulf1-treated heparin reduces binding by two-five fold (FIG. 5B-C), indicating that QSulf1 digestion reduces the capacity of heparin to promote ternary complex formation. Since QSulf1 has substrate specificity towards a subset of 6-O sulfated disaccharides in HS chains (Ai et al., *Journal of Cell Biology* 162, 341-51 (2003)), QSulf1 removes the 6-O sulfate groups that are required for receptor dimerization to promote FGF2-FGFR1 interaction and signaling, but not for FGF2 ligand binding (Schlessinger et al., *Molecular Cell* 6, 743-50 (2000); Lundin et al., *J. of Biol. Chem.* 275, 24653-60 (2000); Pye et al., *J. Biol. Chem.* 273, 22936-42 (1998)).

Figure 6:
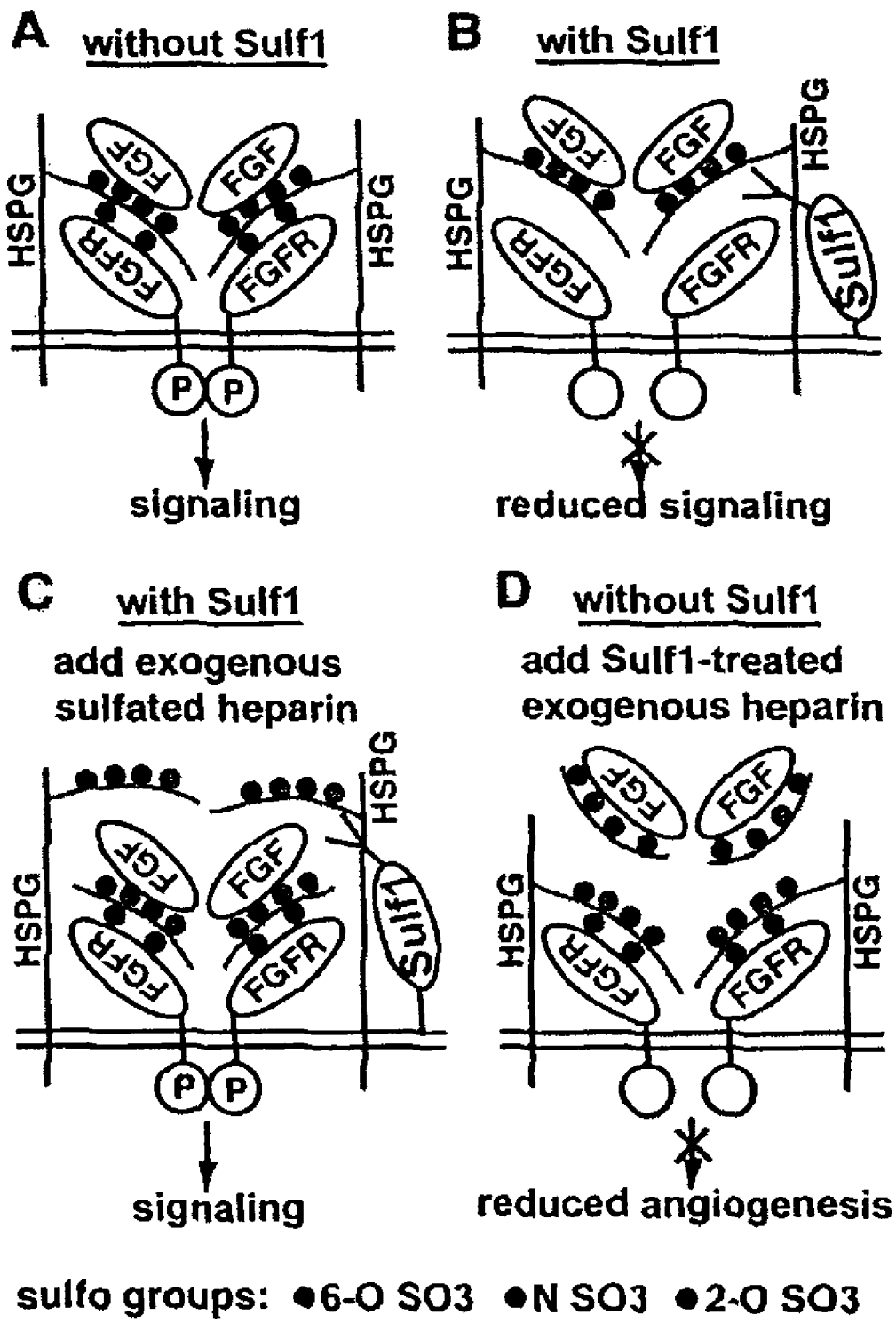
FIG. 6 represents a model of FGF signaling regulation by Sulf1 through modulating FGF ligand-receptor interaction. A 2:2:2 model (two ligands, two HS chains and two receptors) was proposed by others to illustrate ternary complex formation of FGF2-HS-FGFR1 during signaling (Schlessinger et al., *Molecular Cell* 6, 743-50 (2000); Folkman, J., *Semin. Oncol.* 29, 15-18 (2002)). (A) In the absence of Sulf1, sulfated cell surface HS promotes FGF ligand-receptor interaction, receptor dimerization, and activation of intracellular signaling. (B) Selective 6-O desulfation of endogenous HS by QSulf1 reduces FGF ligand-receptor binding, but has little effect on FGF ligand binding to HS. The reduced ligand-receptor interaction suppresses receptor dimerization and signaling. (C) Exogenous sulfated heparin rescues signaling by replacing QSulf1-desulfated endogenous cell surface HS and promoting FGF ligand-receptor interaction. (D) Sulf1 6-O desulfated exogenous heparin has reduced affinity for FGFR1, but competitively binds to FGF2 and interferes with endogenous HS-mediated FGF2 angiogenic activity. The "P" in the intracellular domain of FGFR1 indicates phosphorylation and activation.

In contrast to the results with FGF2, QSulf1 decreases the binding affinity of heparin to the Wnt ligand to enhance Wnt signaling (Ai et al., *Journal of Cell Biology* 162, 341-51 (2003)). QSulf1 is expressed in distinct patterns in multiple lineages of progenitor cells in the early embryo, including somites, floor plate, neural tube and kidney (Dhoot et al., *Science* 293, 1663-6 (2001); Ohto et al., *Genes to Cells* 7, 173-85 (2002)). These QSulf1-expressing progenitor lineages are responding to multiple developmental signals, including Wnts and FGF, for their specification as progenitor lineages. While not wishing to be bound by theory, QSulf1 may functions as a spatial and temporal "switch" with dual regulatory functions to promote Wnt signaling and block FGF signaling in the lineage specification of multipotential embryonic tissues, such as neural tube and somites. Sulf1 orthologs are present in the genomes of a diversity of animals, including *C. elegans, Drosophila* and human (Dhoot et al., *Science* 293, 1663-6 (2001); Morimoto-Tomita et al., *Journal of Biological Chemistry* 277, 49175-85 (2002)), and a second related isoform has been identified in vertebrates, indicating that Sulf1 enzymes are highly conserved during evolution and may regulate FGF and other developmental signals in multiple systems. These studies lay the groundwork for future investigations of the developmental signaling functions of QSulf1 in embryos.

v) QSulf1-mediated HS modification regulates FGF2 ligand-receptor interactions and receptor activation. These studies of QSulf1 regulation of FGF2-heparin-FGFR1 ternary complex formation provide a basis for interpreting the finding that QSulf1 inhibits of FGF2 signaling in mesoderm induction and angiogenesis (FIG. 6). Cell surface HSPGs are well-known cofactors for FGF2 ligand-receptor interactions, controlling receptor dimerization and activation of intracellular signal transduction (Ornitz & Itoh, *Genome Biology* 2, REVIEWS3005 (2001)). The sulfation states of HS are also critical for its FGF2 signaling functions. HS 2-O sulfation is required for FGF2 ligand binding and 6-O sulfation required for receptor binding/dimerization (Lundin et al., *J. of Biol. Chem.* 275, 24653-60 (2000); Pye et al., *J. Biol. Chem.* 273, 22936-42 (1998)), forming an FGF2-HS-FGFR1 ternary complex (FIG. 6A). Studies reported herein demonstrate that QSulf1 6-O endosulfatase activity blocks FGF2 signaling by specific 6-O desulfation of cell surface HS, a modification that inhibits ligand-receptor ternary complex formation and receptor dimerization. This conclusion is supported by the finding that activated forms of FGFR1 are insensitive to the inhibitory activity of QSulf1 (FIG. 6B). Furthermore, the inhibitory activity of QSulf1 in animal cap cells can be rescued by exogenous soluble heparin. Heparin contains an abundance of 6-O sulfated residues, thus replacing the 6-O desulfated HS chains on QSulf1-expressing cells to allow FGF2-FGFR1 complex formation and receptor dimerization (FIG. 6C). It is also demonstrated herein that QSulf1 can be used to enzymatically modify heparin to produce a potent soluble inhibitor of FGF2 signaling in angiogenesis. Inhibitory heparin produced by QSulf1 digestion likely are 6-O desulfated polysaccharides that bind to FGF2, but not to FGFR1, thus competing with endogenous HS on the cell surface to block ternary complex formation and inhibit angiogenesis (FIG. 6D).

In addition to its function in embryos, Sulf1 is also expressed in adult tissues and likely functions in pathophysiological processes such as cancer. Recent studies show HSulf1 expression is suppressed in ovarian cancer cells, and that HSulf1 overexpression in these cancer cells blocks ERK activation by FGF2 and EGF and inhibits proliferation (Lai et al., *J. Biol. Chem.* 278, 23107-23117 (2003)). The growth factor signaling functions of QSulf1 in cells are based on its enzymatic activity and specificity for 6-O desulfation of HS chains. Furthermore, QSulf1 can enzymatically modify soluble heparin to produce potent inhibitors of angiogenesis. These findings, and the specificity of QSulf1 for HS domains involved in ligand receptor interactions, indicate that QSulf1 enzyme will be a useful reagent to generate heparin-based compounds, both in vivo and in vitro. These modified heparin may be useful as therapeutic agents to promote stem cell production for tissue and organ regeneration, and to control tumor cell growth and angiogenesis in the treatment of specific cancers (Folkman, J., *Semin. Oncol.* 29, 15-18 (2002)).

The invention claimed is:

1. A method for inhibiting FGF signaling in an FGF-responsive cell, wherein the FGF signaling inhibited is FGF4-FGFR1 signaling, the method comprising contacting the FGF-responsive cell with an exogenous Sulf1-treated heparin compound, the exogenous Sulf1-treated heparin compound being characterized by the ability to reduce binding of FGF4 to FGFR1.

2. The method of claim 1 wherein the contact with the FGF-responsive cell is in vivo.

3. The method of claim 1 wherein the inhibition of FGF signaling results in an inhibition of angiogenesis.

4. The method of claim 1 wherein the inhibition of FGF signaling results in an inhibition of mesoderm formation.

5. The method of claim 1 wherein the FGF-responsive cell comprise one or more stem cells.

6. The method of claim 5 wherein the inhibition of FGF signaling results in promoting stem cell production.

7. The method of claim 5 wherein the inhibition of FGF signaling results in inhibiting tumor cell growth.

8. The method of claim 1 wherein the exogenous Sulf1-treated heparin is characterized by the removal of at least a subset of the heparin 6-O sulfate groups.

9. The method of claim 1 wherein the exogenous Sulf1-treated heparin prevents FGF4-heparan sulfate-FGFR1 ternary complex formation.

10. The method of claim 1 wherein the exogenous Sulf1-treated heparin compound prevents FGFR1 dimerization.

11. The method of claim 1 wherein the inhibition of FGF signaling results in a decrease in FGF receptor tyrosine kinase activity.

12. The method of claim 11 wherein the decrease in FGF receptor tyrosine kinase activity results in an inhibition of activation of downstream FGF receptor tyrosine kinase targets.

13. The method of claim 12 wherein the downstream FGF receptor tyrosine kinase target is Ras.

* * * * *

UNITED STATES PATENT AND TRADEMARK OFFICE
CERTIFICATE OF CORRECTION

PATENT NO. : 7,968,527 B2
APPLICATION NO. : 11/057390
DATED : June 28, 2011
INVENTOR(S) : Charles P. Emerson, Jr. and Xingbin Ai It is certified that error appears in the above-identified patent and that said Letters Patent is hereby corrected as shown below:

In the Specifications

In Column 1, line 11, please delete "under HD Grant Number 7 R 37 HD007796-33 awarded to C. Emerson, Jr." and insert -- under Grant Nos. DK007006 and HD007796, awarded by the National Institutes of Health. --

Signed and Sealed this
Twenty-eighth Day of May, 2013

Teresa Stanek Rea
*Acting Director of the United States Patent and Trademark Office*